United States Patent [19]

Rex

[11] 4,119,403

[45] Oct. 10, 1978

[54] METHOD AND APPARATUS FOR TEMPERATURE CONTROLLED SAMPLERS

[75] Inventor: John Walter Rex, Pittsburgh, Pa.

[73] Assignee: W. R. Grace & Co., New York, N.Y.

[21] Appl. No.: 806,645

[22] Filed: Jun. 15, 1977

[51] Int. Cl.² .............................................. G01N 31/06
[52] U.S. Cl. ..................................... 23/232 R; 422/83; 422/93
[58] Field of Search ............... 23/232 R, 254 R, 255 R

[56] References Cited

U.S. PATENT DOCUMENTS

| 854,696 | 5/1907 | Jones | 23/255 R |
|---|---|---|---|
| 1,448,901 | 3/1923 | Moreland | 23/254 R |
| 2,669,504 | 2/1954 | Halvorson et al. | 23/232 R X |
| 3,050,372 | 8/1962 | Scott | 23/232 R X |
| 3,352,644 | 11/1967 | Lysyj | 23/232 R |

*Primary Examiner*—Robert M. Reese
*Attorney, Agent, or Firm*—William Kovensky

[57] ABSTRACT

The invention pertains to "wet chemistry" analytical devices for pollutant gases in air. Numerous improvements are provided including a thermo-electric heating/cooling device which uses the atmosphere as a heat sump. Critical flow means to maintain constant pressure throughout the system is also provided.

46 Claims, 8 Drawing Figures

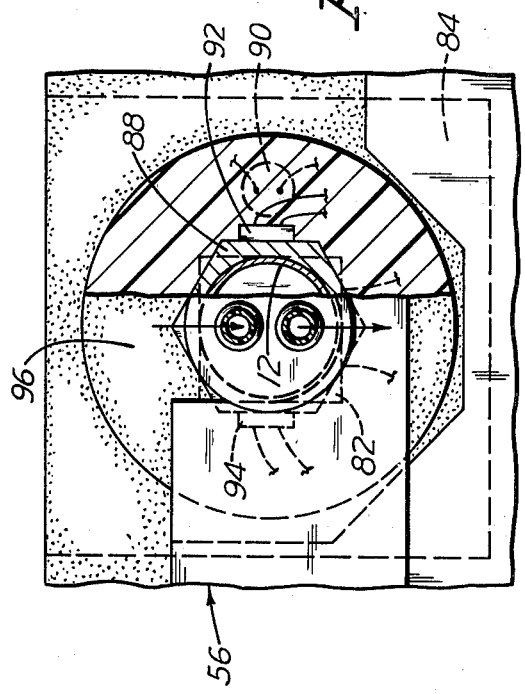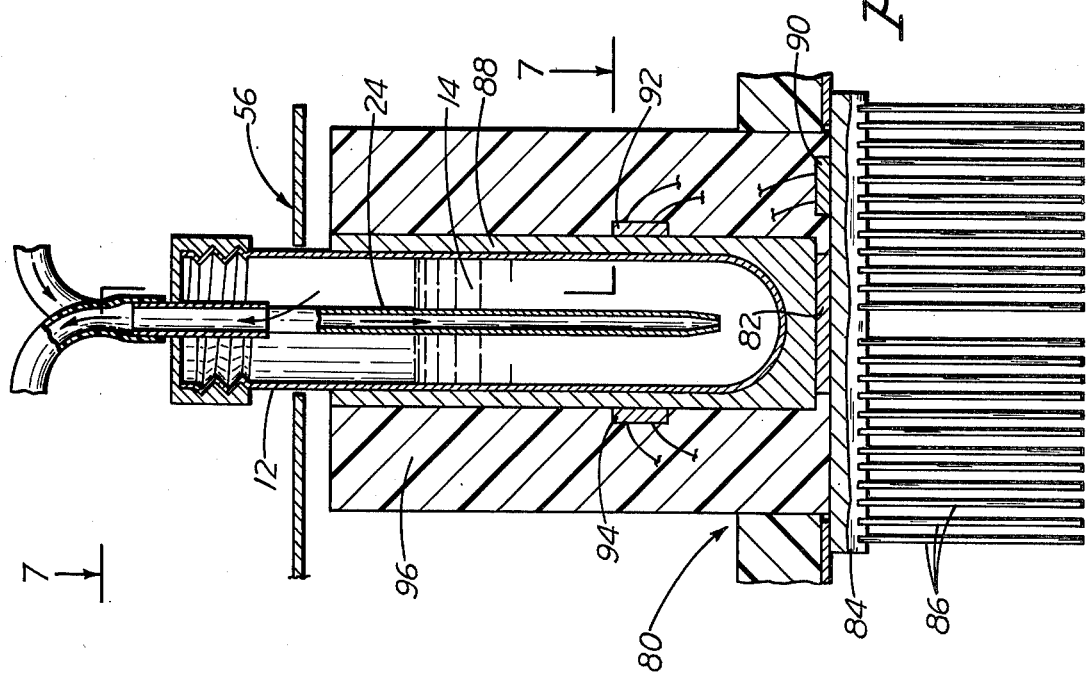

METHOD AND APPARATUS FOR TEMPERATURE CONTROLLED SAMPLERS

This invention pertains to instruments for measuring pollutant gases in air, or more generally, to devices wherein the concentration of one gas in another gas is measured quantitatively. More particularly, the invention pertains to such a sampler wherein at least one sample holder is maintained in a relatively narrow predetermined temperature range using a thermo-electric cooler/heater.

The invention was developed for an air pollution instrument, and more in particular for an instrument to measure the amount of sulfur dioxide in air. $SO_2$ is a particularly sensitive pollutant to measure in that once captured in the absorbing reagent, it is temperature sensitive.

The EPA of the federal government has laid down rules for such instrumentation dictating the temperature range in which the measurement of $SO_2$ in air must be made. Instruments embodying the present invention meet or exceed the EPA specifications for instruments of its type.

Thermo-electric cooler/heaters (hereinafter called "TE" or "TE device") are known, but have not been successfully used in this environment because of the problem of conducting away the heat extracted from the sample by such devices. The invention solves this problem by providing a separate forced air cabinet in which fins associated with the TE are located. In this way, the ambient air is made to move across these fins, the moving ambient air thereby serving as a heat sump when the TE is in a cooling mode and serving as a source of heat when the TE is heating the sample.

The invention provides three temperature zones. The first is ambient which enters the instrument cabinet through louvered walls. The second is the heated reagent zone which is heated above a safe and/or proper operating temperature, in case of freezing temperatures. The third is the TE controlled zone for the $SO_2$ tube. The TE in this third innermost zone uses the first ambient zone as a heat sump, using a fin arrangement, while not affecting the middle zone temperature. A forced air flow in the first zone blows across these fins.

Another feature of the invention is the provision of a pair of bracketing thermostats in close proximity to the reagent whose temperature is being controlled. The two temperatures are made to correspond to the temperature range at which it is desired to hold that sample tube. In the case of $SO_2$, these thermostats have been set at 50° F. and 55° F. respectively. In this manner, rapid temperature changes are avoided. As conditions change the sample tube must go through the center bracketed range before causing a change in the control circuitry and a corresponding reversal of the TE from heating mode to cooling mode or vice versa. Thus, rapid cycling of the TE is avoided, thereby prolonging its useful life and achieving other attendant advantages.

The bracketing thermostats or other temperature sensing means, produce the additional advantage of saving operation time and energy. That is, so long as the temperature of the critical reagent is in the range bracketed by the two thermostats, the TE will not operate at all. Therefore, fast cycling and fast reverses are avoided, while at the same time operating in an energy efficient manner.

Another feature of the invention is the provision of two independent temperature control means, one for the middle zone and one for the sample to be controlled. In this manner, the temperatures at which other pollutant gases are taken is independent of the critical one which is being carefully controlled, and the instrument is independent of ambient temperature, which is particularly important when operating in cold environments.

Another feature of the invention is the provision of critical flow means associated with the overall flow through the instrument. In this manner, the device can be made to operate at a relatively constant pressure, and abnormalities or pulses or fluctuations caused by the pump and surrounding equipment are avoided. The provision of such critical flow means allows the invention to operate at a relatively constant pressure. Two forms of the critical flow means are provided; a hypodermic syringe needle and a glass orifice.

The invention was developed for use with $SO_2$ wherein it is desired to maintain the temperature of the $SO_2$ responsive reagent within a specific range. The invention is equally applicable for use with other materials wherein, for example, it might be desired to remove heat from a tube as in a case where heat is produced by a reaction within the tube. Further, the invention could be used to supply heat, as where heat is necessary to start a reaction or to maintain it or to slow it down. The full range of versatility of the heating means together with the heat sump used in the invention will be evident and will present themselves to those skilled in these arts.

An important advantage of the invention is that it is built of standard components and requires no particularly sophisticated technology in its manufacture. At the same time, there is provided an instrument of the character described which is accurate, rugged, easy to clean and maintain, highly reliable in use and operation, and easily kept up to full operating efficiency.

The above and other advantages of the invention will be pointed out or will become evident in the following detailed description and claims, and in the accompanying drawing also forming a part of the disclosure, in which:

FIG. 6 is a vertical elevational view of the temperature controlled sample portion of the instrument;

FIG. 7 is a cross-sectional view taken on line 7—7 on FIG. 6; and

Figure 3:
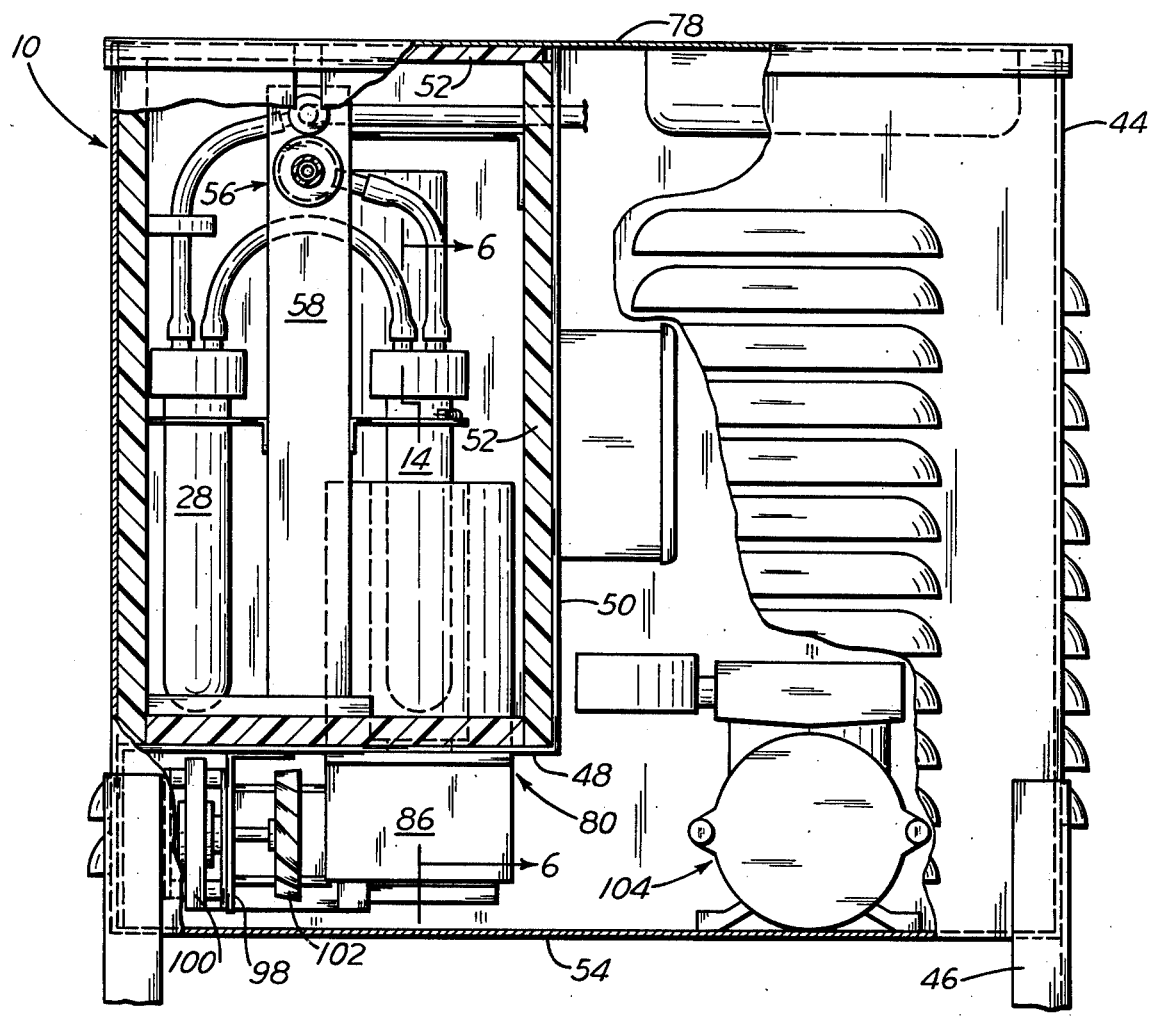
FIG. 3 is a front elevational view with some parts broken away and in cross-section of an instrument embodying the invention.
Figure 4:
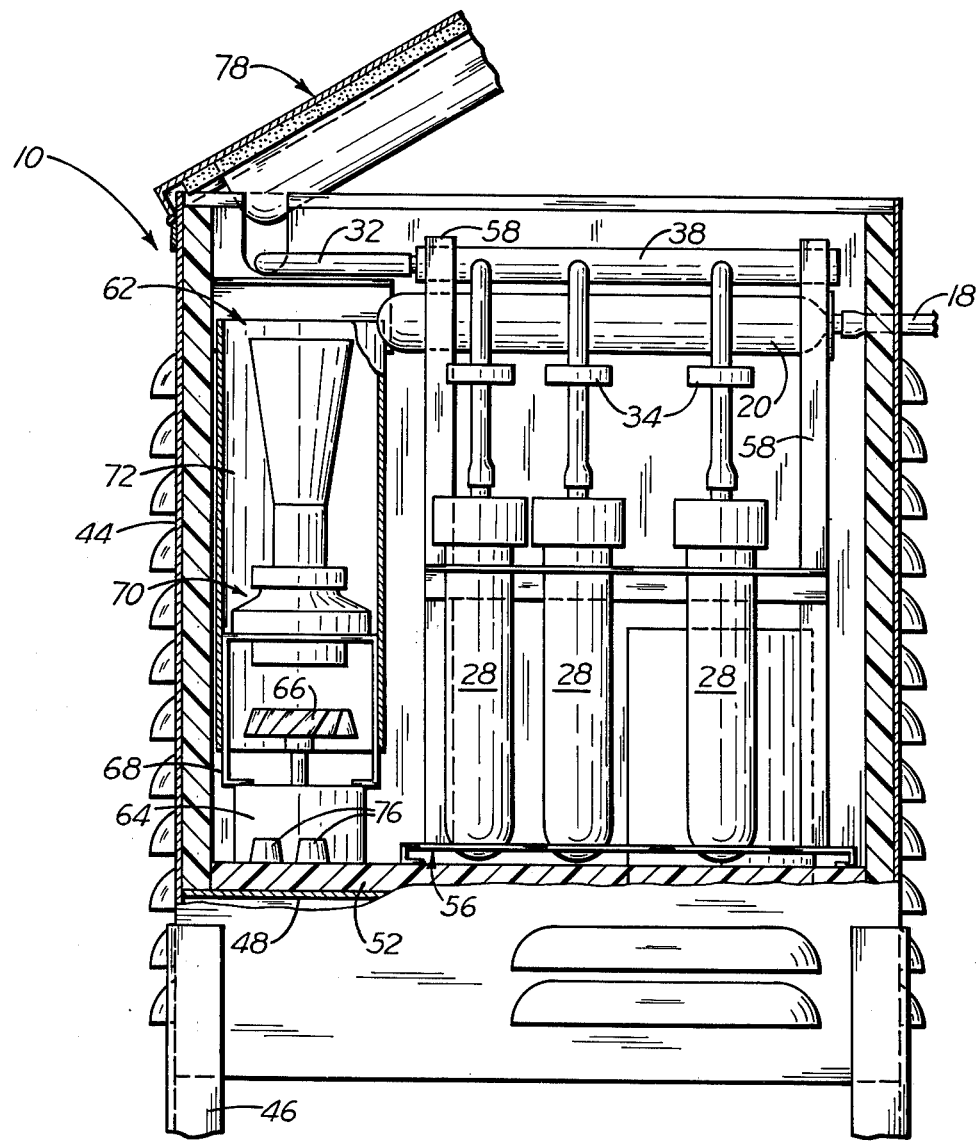
FIG. 4 is a side elevational view taken from the left side of FIG. 3.
Figure 5:
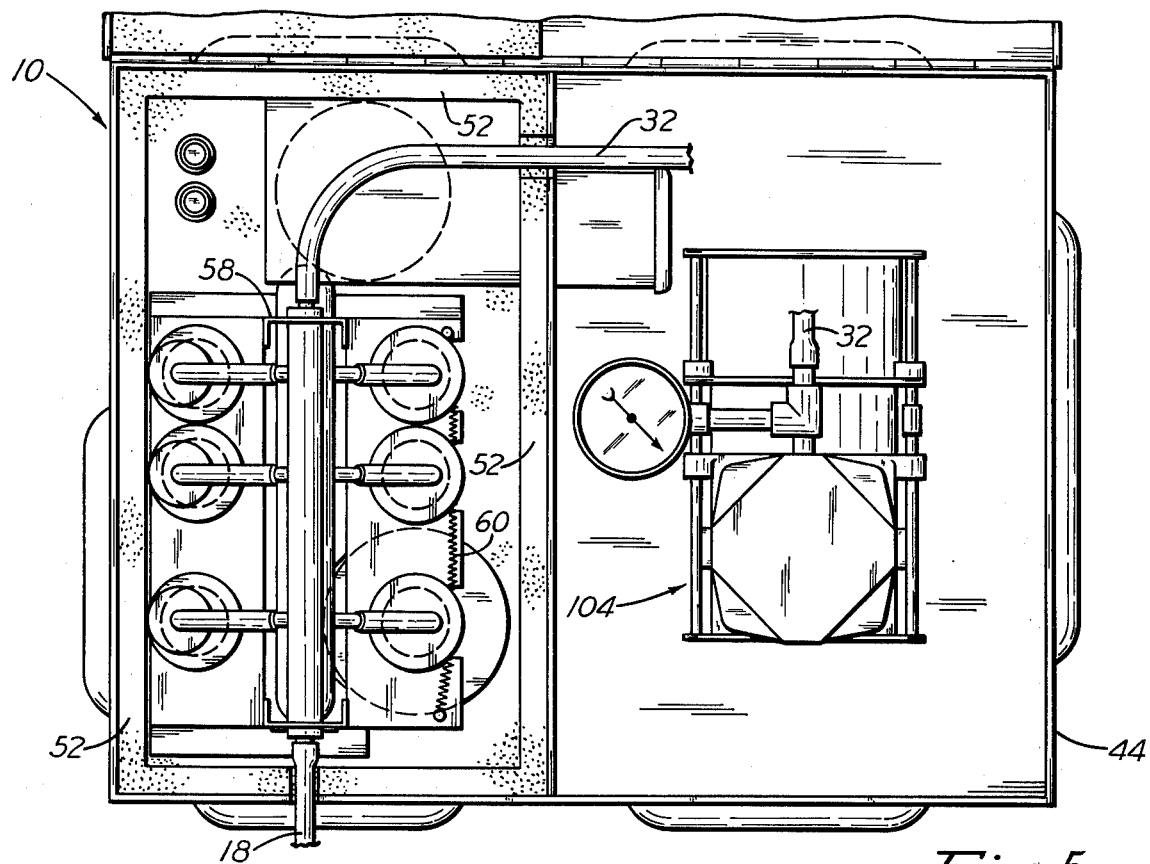
FIG. 5 is a top plan view of the instrument.

An instrument 10 embodying the invention is shown in detail in FIGS. 3, 4 and 5. The principal of operation of the invention is illustrated by the semi-schematic drawing of FIG. 1. Most of the parts shown in FIG. 1 also appear in the other Figures of the drawing.

The basic principal of operation is simple, proven, and well known. A known volume of a sample gas is dispersed through a reagent, usually water based. The reagent is specifically selected to absorb a particular contaminant gas of interest. A manifold is used for the inlet sample gas, usually air, and various taps are made from this intake manifold into the various different tubes containing suitable reagents; one selected for each contaminant gas of interest. The instrument can use standardized, wet chemical techniques, as well as spectrophotometric procedures to quantify the contaminant gases in each tube. Because $SO_2$ is particularly sensitive and subject to degradation while being abosrbed and stored, the improvements of the invention include the provision of temperature control means for the tube which contains the $SO_2$ responsive reagent, to thereby prevent such degradation.

The term "bubbler gas sampler" or "bubbler type" or the like shall be understood to include all the various types and varieties of samples wherein gas flows through liquid. For example, such types would include orifice type bubblers, fritted glass or metal type bubblers, straight tube bubblers, permeation type bubblers, and the like well known varieties.

Figure 1:
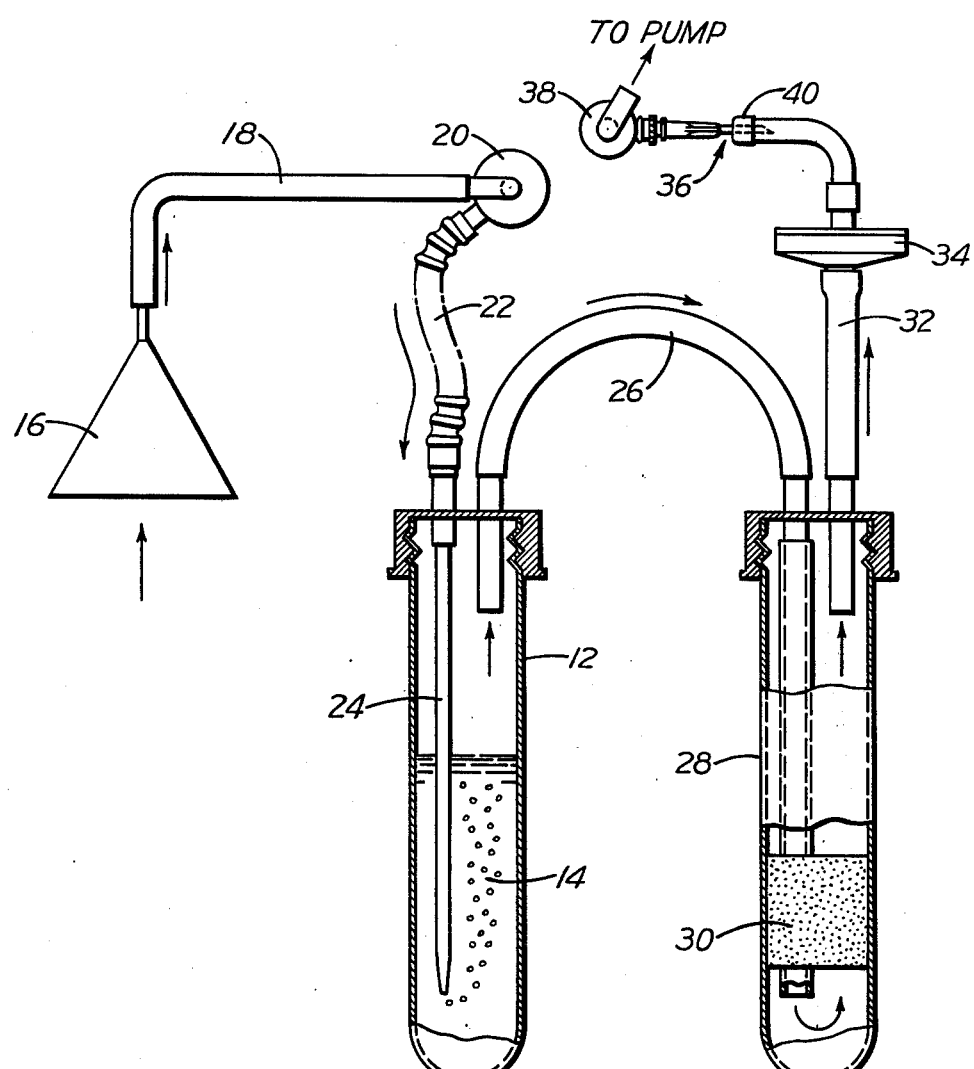
FIG. 1 is a somewhat schematic showing of a portion of an apparatus which illustrates the modus operandi of the gas sampler embodying the invention.

Referring now to FIG. 1, instrument 10 comprises a bubbler tube 12 containing reagent 14. The instrument will include a plurality of such tubes 12, each containing a specific reagent. The $SO_2$ reagent is known as TCM. The tubes may be standard laboratory test tubes; they may be color coded for each of the contaminants. The supply of sample gas containing contaminants, where atmosphere is being sampled, is via a rain shield which may simply comprise a funnel 16 mounted on a tube 18 in an inverted position. The air passes through tubing 18 and thence to an inlet manifold 20. From the inlet manifold, a plurality of lines like the line 22 flow the sample air to the various bubbler tubes 12; a suitable bubbler 24 being provided inside the tube 12, and being mounted by suitable hardware not numbered in the drawing and shown schematically only. Such "plumbing" details are easily within the ability of persons skilled in this art.

The manifold 20 can contain varying numbers of outlets each connected to a flexible tube 22, depending upon how many specific contaminant gases it is desired to test for in the sample stream. In the successfully constructed embodiment, three such outlets were used, however, a sampler for four, five or more contaminants could be made using the teachings of the invention. Manifold 20 is glassware, shown in more detail in the other drawings, and containing the correct number of outlet openings coming out of its side. The drive through the system is by vacuum pump at the exit end of the system, as described in further detail below.

$SO_2$, in particular, is also subject to being adsorbed or absorbed into various materials. For this reason, the invention intake means are all made of selected materials to prevent such chemical and the like degradation of the incoming sample. The funnel and tubing 18 are preferably made of polypropylene, manifold 20 is made of glass, and the connecting tubes 22 are made of Teflon (R). These three materials are generally regarded as suitable for use in probes for handling $SO_2$. It is preferred that no inlet filter, that is upstream of the bubbler 24, be used because such filters together with any particulate matter that collects thereupon could absorb a statistically significant portion of the $SO_2$ in the incoming air sample.

After the bubbler tube 12, a cross-over tube 26 delivers the air to a filter tube 28 which contains a demistor element 30. Element 30 is open cell foam sponge. After the demistor 30, the flow is past the demistor element by an extension of the tube 26 and thence through it and out another tube 32 to another trap 34. The purpose of the dual trap, demistor 30 and trap 34, is to prevent plugging or clogging of the critical flow limiting orifice.

Means are provided to create a critical flow through the system for the purpose of maintaining constant pressure, by elimination of surges, pressure anomalies, and the like which could otherwise enter the system. Two such means are provided. In FIG. 1 there is shown a conventional hypodermic syringe needle arrangement 36, comprising a conventional medical or instrument type syringe needle which is fitted through a sealable membrane provided at the upper end of the tube 32 after the trap 34.

The phenomenon of critical flow is known in the literature. Very briefly, it obtains at a condition wherein the flow of fluid through an orifice produces a ratio of downstream to upstream absolute pressure of 0.528 or less. Using known mathematical and analytical techniques, an orifice size for the needle in the syringe arrangement 36 can be selected to produce a critical flow condition in the entire system. In the successfully constructed embodiment for $SO_2$, a number 27 gauge hypodermic needle 13 mm long was used to maintain a constant rate of approximately 0.2 l/m, and this was maintained independent of pump pressure fluctuations. The pump operated at a nominal pressure of −20 inches Hg. In the successfully constructed embodiment, critical flow means such as the needle of FIG. 1 or the capillary of FIG. 2 was provided for each of the absorption tube pairs thereby maintaining the entire system at the critical pressure. Reference may be had to the Chemical Engineer's Handbook, published by McGraw-Hill of N.Y., Copyright 1950, at page 403, for a more indepth explanation of critical flow, orifice size, temperature, pressure and the like using Fliegner's equation for air.

Figure 2:
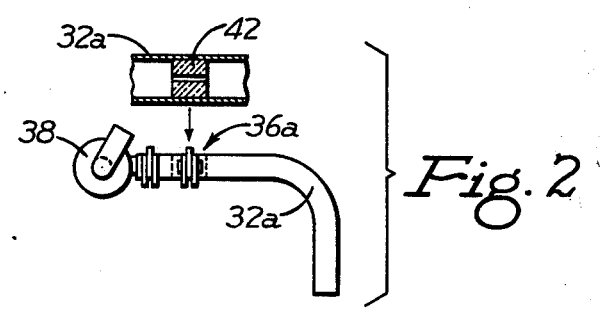
FIG. 2 is a showing of a second embodiment of the critical flow means shown in FIG. 1.

After the critical flow means 36 or 36a of FIG. 2, each of the tubing pairs terminates at an exhaust manifold 38. The outlet end of the exhaust manifold is connected to a vacuum pump 104 described below which provides the driving force for the entire system starting from the intake 16.

The cap member 40 forming part of the critical flow means 36 is a conventional serum cap or membrane, as is used for medical purposes to seal vials of substances to be injected. Because such diaphragms are not intended to be repeatedly used, it is recommended that the cap 40 be changed each time the needle is removed for cleaning, changing needles, or the like.

Referring now to FIG. 2, there is shown a second embodiment of the critical flow means 36a attached to a slightly modified tubing 32a after the filter 34. This means is simply a predetermined diameter orifice, preferably in glass. Functionally, as shown in the exploded part of FIG. 2, these means comprise simply a block of glass 42 formed with a through opening of predetermined small size, in effect, a capillary tube. Reference may be had to an article by C. Huyjen entitled "Use of Glass Capillaries as Critical Orifices" found in the journal of APCA, volume 20, number 10, October 1970, page 675. Use of the needle type vs. the glass capillary type of critical flow means is largely a matter of personal choice of the user.

Referring now in detail to FIGS. 3, 4 and 5, there is shown the successfully constructed embodiment of the invention. Several of the parts described above with regard to FIG. 1 appear in these and the other drawings and the same reference numerals will be used to the extent possible. The invention is contained in a cabinet 44 which is mounted on legs 46. A portion of the space within cabinet 44 is partitioned off by a false bottom wall 48 and a sidewall 50 which define a space for the sample carrier itself. This smaller space is fully insulated on all sides by insulation 52. In the successfully constructed embodiment, Ethofoam (R) boards were used as the insulation. The bottom wall 48 of the insulated space is in spaced relation to the bottom wall 54 of the cabinet 44 for a reason which will appear below.

Means are provided to facilitate the simple removal of all the tubes 14 and 28 from the instrument, together with the two manifolds 20 and 38 and the interconnects between the manifolds and the tubes. To this end, a sheet metal rack 56 is provided. The rack uprights 58 are formed with suitable openings for the two manifolds 20 and 38, see especially FIG. 4. The rack, carrying the manifolds and tubes, can be removed from the instrument by simply disconnecting the two tubings 18 and 32 from their respective manifolds 20 and 38. Thereafter, a user can grasp the outlet manifold 38 and lift the entire rack with manifolds and tubes out of the instrument for cleaning, changing reagents, and the like routine servicing. The rack also carries a "soft spring" 60, see FIG. 5, which holds the reagent tubes 12 snugly in place while at the same time facilitating their easy removal by undoing the spring as the reagent tubes must be handled more frequently than the filter tubes 28.

There is provided within cabinet 44 three separate and distinct temperature zones. The largest zone is the space within the cabinet but outside the sample carrier portion which is essentially at ambient conditions, that is, the outside atmosphere. This zone acts as the heat sump for the third zone. The second zone is the space within the insulated portion, that is within the walls 48, 50 and the insulation 52, with the exception of the third zone. This space is independently heated so the invention can be used in very cold environments. The third zone is a very small zone immediately surrounding one of the tubes, in the successfully constructed embodiment that tube which contains the $SO_2$ responsive reagent. This is the thermo-electrically controlled tube zone, the details of which are shown in FIGS. 6 and 7 and described below. The first zone, that is the area of the cabinet outside the insulated portion in the ambient atmosphere, acts as a heat sump for this third zone using the thermo-electric cooler/heater, as will be described below. Heat flows via the TE between the first and third zones, through the middle or second zone, with no effect on that second zone.

The reagent tube or second zone heating means 62 comprise an adjustable, thermostated, forced air fan blowing across a resistance type heater, whereby a predetermined, minimum heated condition is maintained around the reagents. Heating means 62 assume a safe minimum temperature around the reagents, especially important in cold climates. The details of the heating means 62 are shown in FIG. 4. Reference can be had to the electrical schematic of FIG. 8 and the description thereof below as to operation and connection of heater 62. A motor 64 is mounted on the false bottom wall 48, through the insulation 52 in that vicinity, and this motor drives a simple blade impeller 66. A bracket 68 on the motor 64 carries a cone shaped resistance type heating element. A protective shroud 72 is fitted onto the bracket 68, and extends from a position above the heating element 70 to a position in closely spaced relation above the motor 64. Thus, in operation, the fan 66 will draw air from under the shroud and direct it up through the shroud and over the heating elements 70 to heat the cabinet and a thermostatic control 74 for the heating means 62 located above the shroud, and shown in FIG. 8 only. A pair of fuses 76 for various parts of the circuitry are provided in the insulated cabinet next to the heating means 62, as shown in FIG. 4. The cabinet includes a lid 78. In the successfully constructed embodiment, the heater element 70 was a 100 watt resistance coil heater, with a screw-in, bulb-type base, and the assemblage indicated at 70 in the drawing includes that base which is mounted on the bracket 68.

The third zone temperature is controlled by a thermo-electric heating/cooling device 80 which is mounted in the false bottom 48. This device is shown in FIG. 3 and in greater detail in FIGS. 6 and 7, which three figures should be followed as this portion of the description progresses.

TE 80 is built around a Peltier effect device or platen 82. Such devices are commercially available. In the successfully constructed embodiment, a model CPI. 4-71-06 made by Melcor of Trenton, New Jersey was used. For purposes of this disclosure, it is sufficient to understand that this device will produce heat when DC current flows through it in one direction, and will flow heat away from itself or cool when DC flows through it in the opposite direction. Device 82 is mounted on another block 84 in which are mounted a relatively large plurality of fins 86. The parts 82, 84 and 86 are purchased as an assembled unit. A metal block or heat exchanger 88 is mounted on the top surface of the thermo-electric element 82, and this block 88 is formed with a cavity adapted to snugly receive a standard bubbler type 12 of the type described above. The apparatus is otherwise the same as the other tubes 12 described above, and therefore that description need not be repeated, it being understood that all the tubes are the same, anyone can be used with the TE. A temperature sensing device 90 is mounted on the heat sink block 84, and a pair of temperature sensing devices 92 and 94 are mounted on the heat exchanger block 88; their functioning will be explained below with regard to the circuit diagram of FIG. 8.

The block 84 together with the fins 86 thus act as a heat sump for the thermo-electric device 82. Thus the term "heat sump" and the like as used in the specification and claims herein, shall be understood to mean any such device associated with a source of heating/cooling which can be used in the invention. A relatively thick cylindrical block of temperature insulating material 96 is provided around the heat exchanger 88 in order to carefully maintain the temperature of the reagent within the selected tube 12. Polyurethane was used, but any non-hydroscopic, high insulating factor material will suffice.

Means are provided to force a flow of air across the fins 86 to enhance their operation as a heat sink. The fins 86 both take heat out of the ambient air when TE 80 is operating as a heater, and moves heat into the flowing air over the fins when the TE is operating in its cooling mode. Referring especially to FIG. 3, these means comprise a frame 98 affixed to the bottom side of the bottom wall 48. A motor 100 mounted on this frame drives a fan 102. Thus, fan 102 moves air across the fins 86, the air being drawn through the louvers in the walls of the cabinet 44.

As stated above, the entire flow through the tubes 12 and 28 is under vacuum and the driving force is provided by a vacuum pump 104, which is a standard commercially available component. The pump 104 is in the cabinet 44 and positioned in general alignment with the fan 102 whereby this fan does double duty of both providing the air flow for the heat sinking purposes of the fins 86 as described above, and at the same time directing this flow across the pump motor 104 to cool this device in use.

Figure 8:
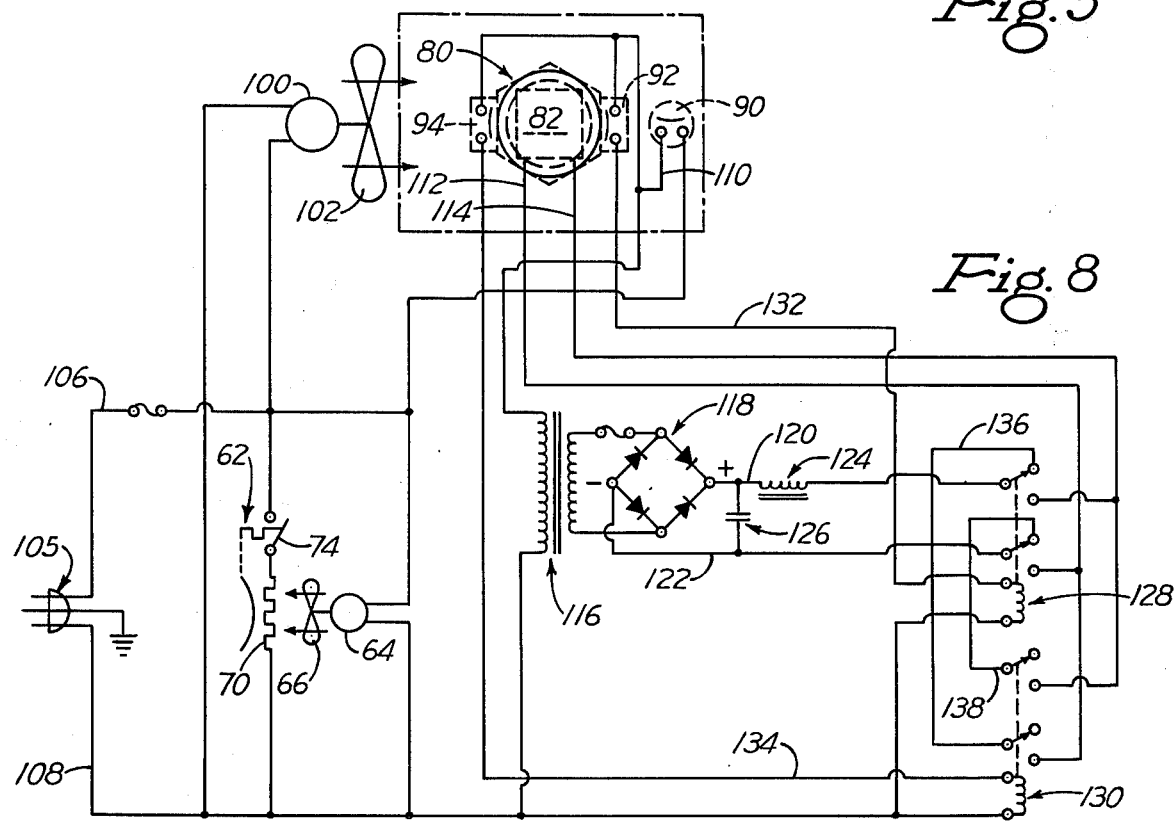
FIG. 8 is an electrical schematic.

FIG. 8 shows the electrical schematic diagram of the successfully constructed preferred embodiment. A standard grounded plug 105 activates a fused power line 106 and a return line 108. The motor 100 for the fan 102 and the motor 64 for the fan 66 are connected directly across the lines 106 and 108 so that they are on to flow ambient air through the cabinet and across the TE fins whenever the device is activated. The resistance heater 70 per se, is activated only when the control 74, responsive to ambient temperature conditions in the cabinet, demands additional heat. Line 106 terminates at one side of the device 90, and another line 110 powers the remaining parts of the circuit thereafter as will be described below. Device 90 is basically a safety device; it is normally closed, opening when the temperature of the TE 80 exceeds a predetermined safe limit, 175° F. in the successfully constructed embodiment, to thereby disable the remainder of the circuitry powered off of the line 110.

Line 110 delivers power to one side of each of the thermostats 92 and 94. A pair of lines 112 and 114 extend away from the TE to the control circuitry described below.

The remaining portions of the circuit of FIG. 8 are driven from a transformer 116, the primary coil of which is connected across the lines 108 and 110, and the secondary coil of which powers a diode rectifier bridge, or other suitable DC producing means 118. A pair of lines 120 and 122 come off of the bridge 118; line 122 is DC negative, and line 120 is DC positive. The two lines 120 and 122 contain an inductor or coil 124 and a capacitor 126 provided to filter the DC power.

The control circuitry is completed by a pair of multi-contact relays 128 and 130. The coil of the relay 128 is connected between a line 132 from the other side of thermostat 92 and the power return line 108. The coil of the relay 130 is connected in a similar sort of circuit between a line 134 from the other thermostat 94 and line 108. The DC power lines 120 and 122 are connected to the common points of the two relay contacts on the relay 128. One side of each of these relay contacts, the normally closed when deactivated sides, are connected by a pair of jumper lines 136 and 138 respectively to the common points of the relay contacts of the other relay 130. The two lines 112 and 114 from the platen 82 in the TE 80 are connected to the normally open or deactivated sides of these respective relay contacts, as shown in FIG. 8.

OPERATION

The flow of gases through the system can be best understood from FIG. 1 and the description above. Basically, the pump 104 puts vacuum on the system, the flow is held constant by the critical flow means, i.e., the needle arrangement 36 of FIG. 1 or the orifice arrangement 36a of FIG. 2. The various bubblers, traps, filters, and manifolds all operate in their conventional manners.

The remainder of the operation of the preferred embodiment can be understood with reference to the electrical schematic of FIG. 8. Both fans 66 and 102 are in constant operation, and heating means 62 maintains a predetermined minimum temperature within the cabinet. TE 80 will maintain its tube at a predetermined temperature between the range determined by the two thermostats 92 and 94.

In the successfully constructed embodiment the thermostat 94 is known as the heating thermostat and is designed to close its contacts, on temperature fall, at approximately 50° F. and thus supply DC power to the TE module 80 in the proper polarity to cause the TE module to supply heat to its tube to prevent freezing.

The other thermostat 92, the cooling thermostat, is designed to close its contacts, on temperature rise, at approximately 55° F. and thus supply DC power to the TE module 80 in the proper polarity (reverse of heating) to cause the TE module 80 to extract heat from its tube to prevent over heating in warm ambient temperature conditions. Thus so long as the temperature of the tube 12 inside the heat exchanger 88 is between 50° and 55° F., the relays 128 and 130 will be at rest and in the position shown in the drawing. So long as the temperature does not go above that set on the device 90, which was 175° F. in the successfully constructed embodiment, the normally closed device 90 remains closed.

If the temperature should fall below the 50°, which means heating is required, thermostat 94 will operate the coil of the relay 130, moving the contects thereof to the opposite condition shown. Operation of the thermostat 94 will cause operation of the relay 130 but not the relay 128. With the relay 130 activated, heating only being required, then the paths through the relay contects are established such that the positive line 120 is connected to the line 112 to the TE and its other line 114 is connected to the negative line 122. If the temperature rises above 55°, then the normally open thermostat 92 will close, thereby causing operation of the relay 128, the relay 130 being non-activated, since the temperature is above 50°. With relay 130 non-activated and relay 128 activated, the positive line 120 is now connected to the opposite side, i.e., to the line 114, the line 112 being connected to the negative line 122 along a path which can be traced through the activated relay 128 contacts. The nature of the device 82 as set forth above is such that it will produce heat when the positive direct current is on line 112, and will conduct heat away from itself when line 114 is connected to DC positive.

While the invention has been described in detail above, it is to be understood that this detailed description is by way of example only, and the protection granted is to be limited only within the spirit of the invention and the scope of the following claims.

I claim:

1. In a method of measuring the amount of one gas in another gas using bubblers and reagents each responsive to a particular gas in which the temperature of one reagent is controlled to be within a predetermined temperature range, the improvements in controlling the temperature of said one reagent comprising the steps of establishing a first ambient temperature zone, establishing a second temperature zone containing the bubblers and reagents, establishing a third controlled temperature zone within said second zone containing said one of said reagents, and using said first zone as a heat sump for said third zone independently of said second zone.

2. The method of claim 1, and maintaining relatively constant pressure throughout the system.

3. The method of claim 1, and heating said second zone.

4. The method of claim 1, wherein said temperature range is selected so as to not degrade the one gas to which said particular reagent is responsive.

5. The method of claim 1, wherein said particular reagent is responsive to $SO_2$.

6. The method of claim 1, and controlling said third zone temperature with a thermo-electric heating/cooling means and bracketing thermostats in heat exchange relationship with said one reagent.

7. In a bubbler type gas sampler comprising a plurality of reagent tubes in parallel each containing a reagent responsive to a selected one of various components in sample gas flowed through the system, the combination comprising pump means for moving sample gas through all of the tubes in parallel, means to maintain a relatively constant pressure throughout the system, said sampler being contained in a cabinet, means to establish a first temperature zone in said cabinet communicating with the ambient atmosphere, a second temperature zone in said cabinet defined by insulation means and surrounding all of said reagent tubes, and a third temperature zone within said second temperature zone comprising a selected one of said reagent tubes, means to control the temperature of said selected one reagent tube within said third zone, means to heat said second zone, said temperature control means for said third zone extending through said second zone and into said first zone, whereby said first zone acts as a heat sump for the heat to be pumped into or out of said third zone, whereby said first and third zones are in heat flow communication with each other, and whereby said second zone is insulated from both said first and third zones.

8. The combination of claim 7, and means to heat said second zone.

9. The combination of claim 7, and temperature sensing means comprising first and second thermostats in heat exchange relationship with said reagent tube, and said thermostats operating at different predetermined temperatures to thereby define a predetermined temperature range within which the temperature of said reagent tube will be held.

10. The combination of claim 1, said temperature control means comprising thermo-electric heating/cooling means in a heat exchange relationship with said selected reagent tube, means to sense the temperature of said reagent tube, control means interposed between said temperature sensor means and said thermo-electric heating/cooling means, said temperature sensor means operating said thermo-electric heating/cooling means via said control means so as to maintain the temperature of said reagent tube within a predetermined temperature range.

11. The combination of claim 9, wherein said thermo-electric heating/cooling means comprises a plurality of fins extending from a block and a thermo-electric member on said block on the side thereof opposite said fins, said thermo-electric member being in said third zone and said fins being in said first zone, means to flow air across said fins, whereby said fins serve to remove heat from the first zone ambient air and to supply said heat to said thermo-electric member when said thermo-electric heating/cooling means is in a heating mode, and wherein said fins serve to put heat into the air flowing thereover when said thermo-electric member is in a cooling mode.

12. The combination of claim 7, wherein said selected gas is $SO_2$, said temperature control means comprising thermo-electric heating/cooling means in heat exchange relation with said selected tube in said third zone and with said first zone, D.C. power supply means, and means to connect said D.C. power supply means to said thermo-electric heating/cooling means in either a heating or cooling relation thereto in order to maintain the temperature in a predetermined range.

13. The combination of claim 12, said last mentioned means comprising a pair of bracketing thermostats adapted to sense the temperature of said selected reagent tube, said means further comprising control means including a plurality of relays interconnected between said D.C. power supply means and said thermo-electric heating/cooling means, said plurality of relays being operated by said bracketing thermostats to achieve said aforementioned mode of operation.

14. The combination of claim 7, and trap means associated with each of said reagent tubes, an inlet manifold to supply sample gas to all of said reagent tubes, an outlet manifold connected to all of said trap means, crossover means from each of said reagent tubes to its associated trap means, a rack mounting all of said tubes, trap means, manifolds and crossover means on said rack, whereby all of said tubes, trap means, manifolds and crossover tubes may be removed from said sampler second zone by simply disconnecting the inlet and outlet means to said inlet and outlet manifolds respectively, whereby cleaning, maintenance and the like of the sample handling portions of the sampler are facilitated.

15. The combination of claim 14, wherein first mentioned selected component is $SO_2$ and wherein all of said tubes and other portions of the tubes, trap means, manifolds and other portions of said apparatus which come into contact with the sample gas are made of glass and other materials which have no effect upon $SO_2$.

16. The combination of claim 7, and means to maintain a relatively constant pressure throughout the system.

17. The combination of claim 16, said sampler including pump means for drawing sample gas through all of said liquid reagent filled tubes, and said constant pressure means comprising critical flow means operatively cooperative with said pump means and said bubbler.

18. The combination of claim 17, said critical flow means comprising a hypodermic syringe needle having a predetermined inside diameter.

19. The combination of claim 17, said critical flow means comprising a glass orifice of a predetermined inside diameter.

20. In a bubbler gas sampler of the type wherein sample gas is flowed through a liquid reagent responsive to a selected component in the sample gas, the improvement comprising thermo-electric heating/cooling means in heat exchange relationship with said reagent, means to sense the temperature of said reagent, control circuit means interposed between said temperature sensor means and said thermo-electric heating/cooling means, said temperature sensor means operating said thermo-electric heating/cooling means via said control circuit means so as to maintain the temperature of said reagent within a predetermined temperature range, and heat sump means in heat exchange relationship with said thermo-electric heating/cooling means.

21. The combination of claim 20, said temperature sensing means comprising first and second thermostats in heat exchange relationship with said reagent, and said thermostats operating at different predetermined temperatures, whereby the temperature difference between said predetermined temperatures determines said predetermined temperature range within which the temperature of said tube will be held.

22. The combination of claim 20, wherein said selected component is $SO_2$, said control means comprising a pair of bracketing thermostats adapted to sense the temperature of said selected reagent, D.C. power supply means, and a plurality of relays interconnected between said D.C. power supply means and said thermo-electric heating/cooling means, and said plurality of relays being operated by said bracketing thermostats to achieve said aforementioned mode of operation.

23. The combination of claim 20, wherein said heat sump means comprises a plurality of fins extending from a block, said thermo-electric heating/cooling means comprising a thermo-electric member on said block on the side thereof opposite said fins, means to flow air across said fins, whereby said fins serve to remove heat from the ambient air and so supply said heat to said thermo-electric member when said thermo-electric heating/cooling means is in a heating mode, and wherein said fins serve to put heat into said ambient air flowing thereover when said thermo-electric member is in a cooling mode.

24. The combination of claim 23, said air flow means operating constantly whenever said sampler is on, pump means for flowing said sample gas so arranged that said air flows across said fins and said pump means.

25. The combination of claim 20, said sampler including pump means for drawing sample gas through at least one of said liquid reagent filled tubes, and critical flow means operatively cooperative with said pump means and said bubbler.

26. The combination of claim 25, said critical flow means comprising a hypodermic syringe needle having predetermined inside diameter.

27. The combination of claim 25, said critical flow means comprising a glass orifice of a predetermined diameter.

28. The combination of claim 20, wherein said sampler comprises a plurality of said tubes each containing a different liquid reagent responsive to a different selected component in the sample gas, each of said reagent tubes being associated with a trap tube, an inlet manifold to supply sample gas to all of said reagent tubes, an outlet manifold connected to all of said reagent tubes, an outlet manifold connected to all of said trap tubes, crossover means from each of said reagent tubes to its associated trap tube, a rack, means to mount all of said tubes and manifolds and crossover means on said rack, whereby all of said tubes, manifolds and crossover tubes may be removed from said sampler by simply disconnecting the inlet and outlet means to said inlet and outlet manifolds respectively, whereby cleaning, maintenance and the like of the sample handling portions of the sampler are facilitated.

29. The combination of claim 28, said sampler including pump means for drawing sample gas through all of said liquid reagent filled tubes, and critical flow means operatively cooperative with said pump means and said bubbler.

30. The combination of claim 28, wherein said first mentioned selected component is $SO_2$ and wherein all of said tubes and other portions of the tubes, manifolds and other portions of said apparatus which come into contact with the sample gas are made of glass and other materials which have no effect upon $SO_2$.

31. In combination, a bubbler type gas sampler comprising a plurality of reagent tubes in parallel each containing a reagent responsive to a selected component in sample gas bubbled through the tube, means for moving said sample gas through said tubes in parallel, critical flow means in the sample flow stream for maintaining a relatively constant sample gas pressure through the system regardless of pressure fluctuations in the system, and means to maintain the temperature of at least one said reagents within a predetermined temperature range.

32. The combination of claim 31, wherein each of said reagent tubes is associated with a trap tube, an inlet manifold to supply sample gas to all of said reagent tubes, an outlet manifold connected to all of said trap tubes, crossover means from each of said reagent tubes to its associated trap tube, a rack carrying all of said tubes, manifolds and crossover means, whereby all of said tubes, manifolds and crossover tubes may be removed from said sampler by simply disconnecting the inlet and outlet means to said inlet and outlet manifolds respectively, whereby cleaning, maintenance and the like of the sample handling portions of the sampler are facilitated.

33. The combination of claim 32, wherein said selected reagent is responsive to $SO_2$ and wherein all of said tubes and other portions of the tubes, manifolds and other portions of said apparatus which come into contact with the sample gas are made of glass and other materials which have no effect upon $SO_2$.

34. The combination of claim 31, said sampler including pump means for drawing sample gas through all of said liquid reagent filled tubes, and critical flow means operatively cooperative with said pump means and said bubbler.

35. The combination of claim 34, said critical flow means comprising a glass orifice of a predetermined capillary-like diameter.

36. The combination of claim 34, said critical flow means comprising a hypodermic syringe needle having a predetermined inside diameter.

37. The combination of claim 31, said temperature control means cmprising thermo-electric heating/cooling means in heat exchange relation with said selected reagent tube, D.C. power supply means, and means to connect said D.C. power supply means to said thermo-electric heating/cooling means in either a heating or cooling relation thereto as required in order to maintain said temperature in said predetermined range.

38. The combination of claim 37, said last mentioned means comprising a pair of bracketing thermostats adapted to sense the temperature of said selected reagent tube, said means further comprising control means including a plurality of relays interconnected between said D.C. power supply means and said thermo-electric heating/cooling means, said plurality of relays being operated by said bracketing thermostats to achieve said aforementioned mode of operation.

39. The combination of claim 37, and heat sump means in heat exchange relationship with said thermo-electric heating/cooling means, said heat sump means comprising a plurality of fins extending form a block, said thermo-electric heating/cooling means comprising a thermo-electric member on said block on the side thereof opposite said fins, means to flow air across said fins, whereby said fins serve to remove heat from the ambient air and to supply said heat to said thermo-electric member when said thermo-electric heating/cooling means is in a heating mode, and wherein said fins serve to put heat into said ambient air flowing thereover when said thermo-electric member is in a cooling mode.

40. The combination of claim 39, said air flow means operating constantly whenever said sampler is on, pump means creating said sample flow, and said air flow also cooling said pump means.

41. A method of measuring the amount of one gas in another gas using bubblers and reagents selected to be responsive to a particular gas, comprising the steps of providing critical flow means for maintaining a relatively constant pressure throughout the system, and maintaining at least one reagent tube within a predetermined temperature range.

42. The method of claim 41, wherein said selected gas of interest is $SO_2$, and wherein said predetermined temperature is selected to prevent degradation of $SO_2$.

43. The method of claim 41, and the step of vacuum drawing sample gas through all of said liquid reagent filled tubes.

44. The method of claim 41, said temperature maintenance means comprising a thermo-electric heating/cooling means, and the steps of putting the operative portion of said thermo-electric heating/cooling means in heat flow communication with said tube and putting heat flow fins for said thermo-electric heating/cooling operative portion in a forced air heat sump.

45. The method of claim 41, and operating said forced air heat sump constantly, and putting the pump means which flows the gas through the system in the path of said forced air to cool said pump means.

46. The method of claim 41, wherein said reagent is responsive to $SO_2$.

* * * * *

UNITED STATES PATENT AND TRADEMARK OFFICE
CERTIFICATE OF CORRECTION

PATENT NO. : 4,119,403
DATED : October 10, 1978
INVENTOR(S) : John Walter Rex

It is certified that error appears in the above-identified patent and that said Letters Patent are hereby corrected as shown below:

On the title page, left hand column, item (73), change the assignee from "W. R. Grace & Co." to --Chemed Corporation--.

Signed and Sealed this

Twenty-seventh Day of February 1979

[SEAL]

Attest:

RUTH C. MASON
*Attesting Officer*

DONALD W. BANNER
*Commissioner of Patents and Trademarks*